United States Patent [19]

Miller

[11] Patent Number: 6,106,871
[45] Date of Patent: Aug. 22, 2000

[54] METHOD FOR INCREASING MILK PRODUCTION IN LACTATING DAIRY CATTLE

[75] Inventor: Bryan Gene Miller, Pine Bush, N.Y.

[73] Assignee: Balchem Corporation, Slate Hill, N.Y.

[21] Appl. No.: 09/363,182

[22] Filed: Jul. 29, 1999

Related U.S. Application Data

[60] Provisional application No. 60/095,441, Aug. 6, 1998.

[51] Int. Cl.⁷ ..................................................... A23K 1/00
[52] U.S. Cl. ............................... 426/2; 426/98; 426/648; 426/807
[58] Field of Search ................................. 426/2, 648, 98, 426/807

[56] References Cited

U.S. PATENT DOCUMENTS

| | | | |
|---|---|---|---|
| 5,145,695 | 9/1992 | Smith et al. | 426/2 |
| 5,204,029 | 4/1993 | Morgan et al. | 264/4.4 |
| 5,310,555 | 5/1994 | Zimmer | 424/438 |
| 5,496,571 | 3/1996 | Blagdon et al. | 426/2 |
| 5,501,857 | 3/1996 | Zimmer | 424/438 |
| 5,571,527 | 11/1996 | Nishimura et al. | 424/438 |
| 5,633,004 | 5/1997 | Nishimura et al. | 424/438 |
| 5,635,198 | 6/1997 | Nishimura et al. | 424/438 |
| 5,686,125 | 11/1997 | Mueller | 426/74 |
| 5,807,594 | 9/1998 | King et al. | |
| 6,022,566 | 2/2000 | Miller | 426/2 |

OTHER PUBLICATIONS

K.B.Atkins, R.A. Erdman and J.H. Vandersall, Dietary Choline Effects on Milk Yield and Duodenal Choline Flow in Dairy Cattle, Journal of Dairy Science, vol. 71, pp. 109–116, 1988.

B.K. Sharma and R.A. Erdman, Effects of High Amounts of Dietary Choline Supplementation on Duodenal Choline Flow and Production Responses of Dairy Cows, Journal of Dairy Science, vol. 71, No. 10, pp. 2670–2676, 1988.

R.A. Erdman and B.K. Sharma, Effect of Dietary Rumen–Protected Choline in Lactating Dairy Cows, Journal of Dairy Science, vol. 74, pp. 1641–1647, 1991.

B.K. Sharma and R.A. Erdman, Effects of Dietary and Abomasally Infused Choline on Milk Production Responses of Lactating Dairy Cows, American Institute of Nutrition, pp. 248–254, 1988.

B.K. Sharma and R.A. Erdman, Abomasal Infusion of Choline and Methionine With Or Without 2–Amino–2–Methyl–1–Propanol for Lactating Dairy Cows, Journal of Dairy Science, vol. 71, pp. 2406–2411, 1988.

R.A. Erdman, R.D. Shaver and J.H. Vandersall, Dietary Choline for the Lactating Cow: Possible Effects on Milk Fat Synethsis, Journal of Dairy Science, vol. 67, pp. 410–415, 1984.

A. Dicostanza and J. N. Spain, "Effect of Rumen Protected Choline or Methionine on Lactational Performance and Blood Metabolites of Periparturine Holsteins" Journal of Dairy Science, vol. 78, No. Supplement 1, p. 188, XP–002121789, 1995.

*Primary Examiner*—Chhaya D. Sayala
*Attorney, Agent, or Firm*—Banner & Witcoff, Ltd.

[57] ABSTRACT

A method increasing milk production in lactating dairy cattle by administering to prepartum cattle a rumen-protected choline compound.

12 Claims, No Drawings

METHOD FOR INCREASING MILK PRODUCTION IN LACTATING DAIRY CATTLE

Benefit of the Aug. 6, 1998 filing date of the provisional application Ser. No. 60/095,441 by the same inventor and entitled "Method For Increasing Milk Production In Lactating Dairy Cattle" is hereby claimed.

BACKGROUND OF THE INVENTION

1. Field of the Invention

The present invention relates to a method for increasing milk production in lactating dairy cattle by administering to dairy cattle, prior to calving and during lactation, a rumen-protected choline compound.

2. Description of the Prior Art

It is an ongoing challenge to increase milk production in lactating dairy cattle. Part of the challenge is ensuring that nutrients and proteins in the ration which may aid in increasing milk production are not broken down in the rumen.

Choline is an essential nutrient for dairy cattle. Normally, choline is provided in adequate quantities as a result of synthesis by ruminal microflora in cattle-feeding programs using primarily forage-based diets. Protozoa appear to be the primary species involved in synthesis of choline. Consequently, diets that result in ruminal conditions which compromise growth and proliferation of protozoa may result in inadequate choline supply to the animal. High-concentrate diets frequently produce ruminal pH in the range of 5.5 to 5.8, which is less than optimal for proliferation of protozoa. Inclusion of fat in the diet may further reduce protozoal populations. This may be the consequence of lower ruminal pH that occurs with fat feeding, or may be due to some direct effect of fat on the protozoa. In any case, diets that induce low protozoa populations may benefit from addition of choline to the diet. Previous research has suggested that choline chloride is extensively degraded in the rumen.

It is known that pure choline chloride fed to ruminants is broken down in the rumen and is an ineffective treatment. It was discovered that encapsulated choline could be used to enable the choline chloride to pass through the rumen without breaking down thus allowing absorption in the gut.

Cattle can suffer ketosis which is associated with large milk production and newly lactating cows. Ketosis results from a deficiency of carbohydrates but is also associated with fat infiltration of the liver. It is believed that choline -has a metabolic effect because of its ability to enhance the liver's capacity to handle (export) fat and fatty acids back out of the liver.

It is known to feed encapsulated choline chloride to lactating dairy cattle as described in U.S. Pat. No. 5,496,571. However, no one has heretofore recognized that feeding choline prior to calving will provide increased milk production after calving.

SUMMARY OF THE INVENTION

The present invention is directed to a method of increasing milk production in lactating dairy cattle by administering to prepartum cattle a rumen-protected choline compound. The present invention is further directed to continuing the administering of rumen-protected choline to cattle during lactation. The rumen-protected choline compound is preferably added directly to ration which is fed to the prepartum cattle.

Although not wishing to be bound by any particular theory, this increased milk production may be the result of preparing the liver to handle the stress and metabolic changes associated with calving, milk production, and shortage of carbohydrates.

The rumen-protected choline compound protects the choline compound against metabolism by bacteria in the rumen of the cattle. This allows controlled amounts of the choline compound to be readily absorbed in the digestive track of the animal.

DETAILED DESCRIPTION OF THE PREFERRED EMBODIMENTS

It was discovered that improvements could be made in milk production in lactating dairy cattle by feeding prepartum cattle a ration which included rumen-protected choline compound. The method of the present invention is directed to delivery to prepartum dairy cattle of ration containing rumen-protected choline in amounts effective to improve milk production. The method of the present invention is also directed to continuing delivery of the ration containing rumen-protected choline after calving. The expected increase is about 5–10 lbs. or more of milk per cow per day.

The choline compound is preferably administered at least about 5 days before calving, more preferably between about 10 and about 28 days before calving, and most preferably about 14 to about 28 days prior to calving. After calving, the choline-chloride is continued for at least about 30 days, preferably at least about 45 days, more preferably between about 45 and about 80 days.

The choline compound is rumen-protected in order to allow the choline to survive the rumen where it would otherwise break down rendering the choline useless. The rumen-protected choline compound is added directly to the ration which is normally fed to cattle. In order to prevent degradation of the choline compound prior to use, it is preferable that the rumen-protected choline compound is not mixed with any other ingredient prior to mixing with the ration. Also preferably, the rumen-protected choline compound is mixed with the ration just prior to feeding the cattle.

The ration may be any suitable ration used to feed prepartum cattle or in diets designed to decrease protozoa growth. Typically the ration contains greater than 25% grain (corn, oats, wheat, milo, barley, etc.) The amount of ration depends on the size and milk yield of the animal and is well within the skill of the art.

The choline compound may be any suitable form of choline. Choline is available in many forms such as choline chloride, choline bitartrate, choline dihydrogencitrate, choline bicarbonate, and choline free base. Choline chloride is preferred.

Any suitable delivery form that protects choline in the rumen and allows it to be readily absorbed in the remainder of the cattle's digestive track, e.g. the abomasum, stomach, and/or gut, is contemplated as being useful in the present invention. That is, any delivery form that protects the choline compound against metabolism by bacteria in the rumen of the ruminant. The delivery form can be, for example, any encapsulated delivery form such as suitable encapsulating compositions described in U.S. Pat. Nos. 4,876,097, 5,190,775, 5,204,029 and 5,496,571, which disclosures are hereby incorporated by reference in their entirety. Suitable protecting or encapsulating means may also include bypass fat, which is fat that bypasses the rumen and thus is not absorbed in the rumen. If encapsulation is used to protect the choline, any of the above forms of choline that are liquids immiscible in the encapsulating media or are readily soluble in a liquid immiscible in the encapsulating media are useful.

Rumen-protected choline is conveniently administered in the normal feed ration and is added to the ration in an amount to provide between about 5 to 20 g per head per day of choline, preferably about 15 g per head per day. The amount of rumen-protected choline added to or supplemented to the ration is based on the amount of choline that can survive the rumen.

The invention will be further described by reference to the following examples. These examples should not be construed in any way as limiting the invention to anything less than that which is disclosed or which could have been obvious to anyone skilled in the art.

EXAMPLES

Example 1

Cattle selected from a 660 head commercial Holstein herd were used to determine the effects of adding choline chloride prepartum. The cattle were kept in free stalls, fed a TMR and milked 3 times per day. The rolling herd average for the herd was 28,800 lbs. (DHIA) Cattle used in the trial were selected on the basis of pairing, or matching control and treatment cows that had similar past histories, i.e. prior milk production, age, number of lactation.

Twenty-one days prior to expected calving date, cows were moved into "transition" groups. These cows were divided into two groups, a control group and a group which received 60 g of CAP-SHURE CHOLINE CHLORIDE mixed into the feed at the bunk with each feeding. Feed intake and subsequent milk production were each measured. Prior to freshening, cattle received the diet listed below as "prepartum," and after freshening they received the diet listed under "Fresh cows" for 50 days.

| Ingredient Composition of Diets Fed | | |
|---|---|---|
| Ingredients | Pre-partum | Fresh Cows |
| Grain/concentrate mix | — | 15.1 |
| Whole Cotton Seed | 2.0 | 5.8 |
| Earlage (38% DM) | 24.8 | 22.0 |
| Propylene Glycol | | 1.2 |
| Corn Silage | 44.4 | 18.1 |
| Alfafa Haylage | | 7.0 |
| Beet Pulp (wet pressed, 25% DM) | | 13.3 |
| Dry Hay #1 | 19.1 | 5.7 |
| Dry Hay #2 | | 5.7 |
| Milk Whey (25% DM) | | 6.0 |
| Prepartum Premix | 9.8 | |
| TOTAL | 100.1 | 99.9 |

| Nutrient Content of Diets Fed | | |
|---|---|---|
| Nutrient Content | Pre-partum | Fresh Cows |
| Dry Matter (%) | 55.6 | 57.2 |
| CP (%) | 15.0 | 16.3 |
| ADF (%) | 25.6 | 22.9 |
| NDF (%) | 34.3 | 34.3 |
| $NE_L$ Mcal/lb | 0.74 | 0.73 |
| Calcium (%) | 1.06 | 0.95 |
| Phosphorus (%) | 0.32 | 0.43 |

Results

Effect of CAP-SHURE CHOLINE CHLORIDE on milk production for cows provided 21 days prior to calving and to Fresh cows.

| | Control | CAP-SHURE CHOLINE CHLORIDE |
|---|---|---|
| Number of Cows | 15 | 6 |
| Avg. Milk Yield (lbs) | 87.5 | 103.4 |
| Fat % | 4.2 | 3.6 |
| Protein % | 3.2 | 3.3 |
| Fat Corrected Milk | 96.2 | 104.9 |
| SCC | 233 K | 63 K |

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A method of increasing milk production in lactating dairy cattle, comprising:

feeding ration containing rumen-protected choline compound to prepartum dairy cattle.

2. The method of claim 1 wherein the choline compound is selected from the group consisting of choline chloride, choline bitartrate, choline dihydrogencitrate, choline bicarbonate, and choline free base.

3. The method of claim 2 wherein the choline compound is choline chloride.

4. The method of claim 1 wherein the rumen-protected choline compound is an encapsulated choline compound.

5. The method of claim 1 wherein between about 5 and about 20 g of choline compound is fed to each head of prepartum cattle per day.

6. The method of claim 5 wherein about 15 g of choline compound is fed to each head of prepartum cattle per day.

7. The method of claim 1 wherein the choline compound is administered to the prepartum cattle at least about 5 days prior to calving.

8. The method of claim 7 wherein the choline compound is administered to the prepartum cattle between about 10 and about 28 days prior to calving.

9. The method of claim 8 wherein the choline compound is administered to the prepartum cattle between about 14 and about 28 days prior to calving.

10. The method of claim 1 wherein the choline compound is also administered postpartum for at least about 30 days after calving.

11. The method of claim 10 wherein the choline compound administered at least about 45 days after calving.

12. The method of claim 11 wherein the choline compound administered between about 45 and about 80 days after calving.

* * * * *